(12) United States Patent

Pasquier et al.

(10) Patent No.: US 7,077,872 B2
(45) Date of Patent: Jul. 18, 2006

(54) OXIDATION HAIR DYES CONTAINING 3-AMINOPHENOL DERIVATIVES, AND NOVEL 3-AMINOPHENOL DERIVATIVES

(75) Inventors: Cècile Pasquier, Marly (CH); Patrick Wyss, Neyruz (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 275 days.

(21) Appl. No.: 10/487,619

(22) PCT Filed: Apr. 24, 2002

(86) PCT No.: PCT/EP02/04490

§ 371 (c)(1),
(2), (4) Date: Feb. 23, 2004

(87) PCT Pub. No.: WO03/017955

PCT Pub. Date: Mar. 6, 2003

(65) Prior Publication Data

US 2004/0200010 A1 Oct. 14, 2004

(30) Foreign Application Priority Data

Aug. 25, 2001 (DE) .................. 101 41 722

(51) Int. Cl.
*A61K 7/13* (2006.01)
(52) U.S. Cl. .............. 8/405; 8/406; 8/408; 8/409; 8/410; 8/411; 8/412; 8/421; 8/423; 8/435; 8/565; 8/566; 8/568; 544/180; 544/224; 546/249
(58) Field of Classification Search .......... 8/405, 8/406, 408, 409, 410, 411, 412, 421, 423, 8/435, 565, 566, 568; 544/180, 224; 546/249
See application file for complete search history.

(56) References Cited

U.S. PATENT DOCUMENTS

| 4,129,414 A | * | 12/1978 | Rose et al. ............ 8/409 |
| 4,838,894 A | * | 6/1989 | Kijek et al. ............ 8/412 |
| 5,019,130 A | | 5/1991 | Flood ................... 8/423 |
| 5,409,503 A | * | 4/1995 | Clausen et al. .......... 8/408 |

FOREIGN PATENT DOCUMENTS

DE 25 18 393 A 11/1976
DE 100 32 134 C 12/2001

OTHER PUBLICATIONS

STIC Search Report (Dec. 9, 2005).*

Jacobsen, et al: "Ueber Das Metaoxyazobenzol und Die . . . ", Chemische Berichte, BD. 36, 1903, pp. 4093-4123, XP002214930.
Hubert-Habart, et al: "Recherches sur les Derives Nitres . . . " Chimie Therapeutique, BD. 8, NR. 3, 1973, pp. 314-318, XP001099069.
Chapter "Protective Groups", in Organic Synthesis, Chapter 3, Wiley Interscience, 1991, pp. 143-174.
Chapter "Protective Groups", in Organic Synthesis, Chapter 7, Wiley Interscience, 1991, pp. 494-653.

* cited by examiner

*Primary Examiner*—Eisa Elhilo
(74) *Attorney, Agent, or Firm*—Michael J. Striker

(57) ABSTRACT

The object of the present patent application are agents for dyeing keratin fibers based on a developer-coupler combination and characterized in that they contain at least one 3-aminophenol derivative of formula (I) or a physiologically compatible, water-soluble salt thereof

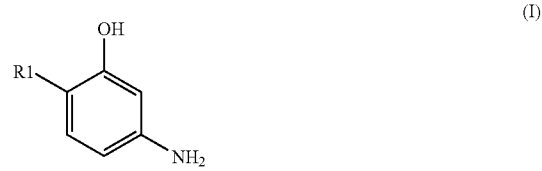

wherein
R1 denotes a group of the formula

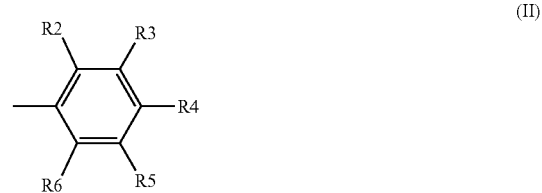

or a group of the formula

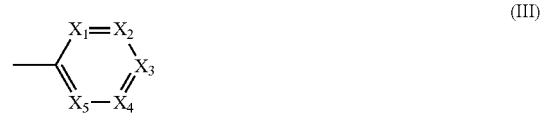

as well as novel 3-aminophenol derivatives.

12 Claims, No Drawings

OXIDATION HAIR DYES CONTAINING 3-AMINOPHENOL DERIVATIVES, AND NOVEL 3-AMINOPHENOL DERIVATIVES

The present invention relates to agents for oxidative dyeing of keratin fibers, particularly human hair, based on a developer/coupler combination containing as the coupler a 3-aminophenol derivative substituted in the 6-position, as well as novel 3-aminophenol derivatives substituted in the 6-position.

Oxidation dyes have attained substantial importance in the field of keratin fiber dyeing and particularly hair dyeing. The color is generated by reaction of certain developers with certain couplers in the presence of an appropriate oxidant. The developers used for this purpose are, in particular, 2,5-diaminotoluene, 2,5-diaminophenylethyl alcohol, p-aminophenol, 1,4-diaminobenzene and 4,5-diamino-1-(2-hydroxyethyl)pyrazole, whereas suitable couplers are, for example, resorcinol, 2-methylresorcinol, 1-naphthol, 3-aminophenol, m-phenylenediamine, 2-amino-4-(2'-hydroxyethyl)aminoanisole, 1,3-diamino-4-(2'-hydroxyethoxy)benzene and 2,4-diamino-5-fluorotoluene.

In addition to being able to produce colors of the desired intensity, oxidation dyes used for dyeing human hair must meet numerous additional requirements. For example, such dyes must be unobjectionable from a toxicological and dermatological standpoint, and the hair colorations obtained must be highly resistant to light, permanent waving, acids and rubbing. In any case, however, in the absence of exposure to light, rubbing and chemical agents such colorations must remain stable for a period of at least 4 to 6 weeks. Moreover, it must be possible, by a combination of suitable developers and couplers, to produce a wide range of different color shades.

Although many couplers are already known, with the currently known colorants it is not possible to meet the requirements placed on a colorant in every respect. Hence, a need continues to exist for novel couplers that will meet the aforesaid requirements to an especially high degree.

We have now found that certain 3-aminophenol derivatives of general formula (I) meet the requirements placed on couplers to an especially high degree and with known developers give intense and unusually light-fast and wash-fast color shades.

Hence, the object of the present invention is an agent for dyeing keratin fibers, for example wool, furs, feathers or hair, particularly human hair, said agent being based on a developer-coupler combination and characterized in that it contains at least one 3-aminophenol derivative of formula (I) or a physiologically compatible, water-soluble salt thereof.

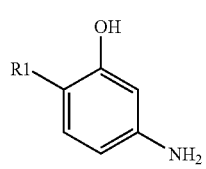

(I)

wherein R1 denotes a group of formula (II) or (If)

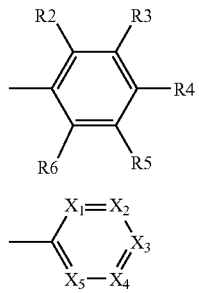

wherein R2, R3, R4, R5 and R6 independently of each other denote hydrogen, a halogen atom (F, Cl, Br, I), a cyano group, a hydroxyl group, a $C_1$–$C_4$-alkoxy group, a phenoxy group, a $C_1$–$C_4$-hydroxyalkoxy group, a $C_1$–$C_6$-alkyl group, a phenyl group, a $C_1$–$C_4$-alkyl thioether group, a mercapto group, a nitro group, an amino group, a $C_1$–$C_4$-alkylamino group, a hydroxy($C_2$–$C_4$)alkylamino group, a di($C_1$–$C_4$) alkylamino group, a di[hydroxy($C_2$–$C_4$)alkyl]amino group, a [dihydroxy($C_3$–$C_4$)alkyl]amino group, a [hydroxy($C_2$–$C_4$) alkyl]-($C_1$–$C_4$)-alkylamino group, a trifluoromethyl group, a —C(O)H group, a —C(O)CH$_3$ group, a —C(O)CF$_3$ group, a —Si(CH$_3$)$_3$ group, a ($C_1$–$C_4$)-hydroxyalkyl group, a ($C_2$–$C_4$)-dihydroxyalkyl group, a ($C_1$–$C_4$)-aminoalkyl group or a ($C_1$–$C_4$)-cyanoalkyl group, or two adjacent R2 to R6 groups form an —O—CH$_2$—O— bridge;

$X_1$, $X_2$, $X_3$, $X_4$ and $X_5$ independently of each other denote nitrogen or a C—R7 group, C—R8 group, C—R9 group, C—R10 group or C—R11 group, provided that at least one and at the most three of the $X_1$ to $X_5$ groups denote nitrogen; and R7, R8, R9, R10 and R11 independently of each other denote hydrogen, a halogen atom (F, Cl, Br, I), a cyano group, a ($C_1$–$C_6$)-alkyl group, a ($C_1$–$C_4$)-alkyl thioether group, a mercapto group, a nitro group, an amino group. a ($C_1$–$C_4$)-alkylamino group, a di($C_1$–$C_4$)alkylamino group, a trifluoromethyl group, a —C(O)H group, a —C(O)CH$_3$ group, a —C(O)CF$_3$ group, a —Si(CH$_3$)$_3$ group, a —C(O)—NH$_2$ group, a ($C_1$–$C_4$)-hydroxyalkyl group or a ($C_2$–$C_4$)-dihydroxyalkyl group.

Compounds of formula (1) are, for example:

4-amino-[1,1'-biphenyl]-2-ol, 4-amino-4'-methyl-[1,1'-biphenyl]-2-ol, 4-amino-3'-methyl-[1,1'-biphenyl]-2-ol, 4-amino-2'-methyl-[1,1'-biphenyl]-2-ol, 4-amino-2',3'-dimethyl-[1,1'-biphenyl]-2-ol, 4-amino-2',4'-dimethyl-[1,1'-biphenyl]-2-ol, 4-amino-2',5'-dimethyl-[1,1'-biphenyl]-2-ol, 4-amino-2',6'-dimethyl-[1,1'-biphenyl]-2-ol, 4-amino-3',4'-dimethyl-[1,1'-biphenyl]-2-ol, 4-amino-3',5'-dimethyl-[1,1'-biphenyl]-2-ol, 4-amino-3',6'-dimethyl-[1,1'-biphenyl]-2-ol, 4-amino-2',4',5'-trimethyl-[1,1'-biphenyl]-2-ol, 4-amino-2',4',6'-trimethyl-[1,1'-biphenyl]-2-ol, 4-amino-2',3',4'-trimethyl-[1,1'-biphenyl]-2-ol, 4-amino-2',3',5'-trimethyl-[1,1'-biphenyl]-2-ol, 4-amino-2',3',6'-trimethyl-[1,1'-biphenyl]-2-ol, 4-amino-4'-chloro-[1,1'-biphenyl]-2-ol, 4-amino-3'-chloro-[1,1'-biphenyl]-2-ol, 4-amino-2'-chloro-[1,1'-biphenyl]-2-ol, 4-amino-4'-fluoro-[1,1'-biphenyl]-2-ol, 4-amino-3'-fluoro-[1,1'-biphenyl]-2-ol, 4-amino-2'-fluoro-[1,1'-biphenyl]-2-ol, 4-amino-4'-bromo-[1,1'-biphenyl]-2-ol, 4-amino-3'-bromo-[1,1'-biphenyl]-2-ol, 4-amino-2'-bromo-[1,1'-biphenyl]-2-ol, 4-amino-3',5'-dichloro-[1,1'-biphenyl]-2-ol, 4-amino-3',5'-difluoro-[1,1'-biphenyl]-2-ol, 4-amino-3'-bromo-5'-methyl-[1,1'-biphenyl]-2-ol, 4-amino-4'-(trifluoromethyl)-[1,1'-biphenyl]-2-ol, 4-amino-3'-(trifluoromethyl)-[1,1'-biphenyl]-2-ol, 4-amino-2'-(trifluoromethyl)-[1,1'-biphenyl]-2-ol, 4-amino-4'-nitro-[1,1'-biphenyl]-2-ol, 4-amino-3'-nitro-[1,1'-biphenyl]-2-ol, 4-amino-2'-nitro-[1,1'-biphenyl]-2-ol, 4-amino-5'-methyl-3'-nitro-[1,1'-biphenyl]-2-ol, 4-amino-4'-methyl-3'-nitro-[1,1'-biphenyl]-2-ol, 4-amino-2'-methyl-3'-nitro-[1,1'-biphenyl]-2-ol, 4-amino-2'-nitro-4'-(trifluoromethyl)[1,1'-biphenyl]-2-ol, 4-amino-3'-nitro-5'-(trifluoromethyl)[1,1'-biphenyl]-2-ol, 4-amino-3'-nitro-4'-(trifluoromethyl)[1,1'-biphenyl]-2-ol, 4-amino-3'-nitro-2'-(trifluoromethyl)[1,1'-biphenyl]-2-ol, 4'-amino-2'-hydroxy-[1,1'-biphenyl]4-carbonitrile, 4'-amino-2'-hydroxy-[1,1'-biphenyl]-3-carbonitrile, 4-amino-4'-methoxy-[1,1'-biphenyl]-2-ol, 4-amino-3'-methoxy-[1,1'-biphenyl]-2-ol, 4-amino-2'-methoxy-[1,1'-biphenyl]-2-ol, 4-amino-4'-ethoxy-[1,1'-biphenyl]-2-ol, 4-amino-3'-ethoxy-[1,1'-biphenyl]-2-ol, 4-amino-2'-ethoxy-[1,1'-biphenyl]-2-ol, 4-amino-3',4'-dimethoxy-[1,1'-biphenyl]-2-ol, 4-amino-3',5'-dimethoxy-[1,1'-biphenyl]-2-ol, 4-amino-2',3'-dimethoxy-[1,1'-biphenyl]-2-ol, 4-amino-2',4'-dimethoxy-[1,1'-biphenyl]-2-ol, 4-amino-2',5'-dimethoxy-[1,1'-biphenyl]-2-ol, 5-amino-2-(1,3-benzodioxol-5-yl)phenol, 4-amino-4'-methoxy-3'-methyl-[1,1'-biphenyl]-2-ol, 4-amino-4'-methoxy-2'-nitro-[1,1'-biphenyl]-2-ol, 4-amino-4'-methoxy-[1,1'-biphenyl]-2-ol, 4-amino-4'-phenoxy-[1,1'-biphenyl]-2-ol, 4-amino-4'-methylthio-[1,1'-biphenyl]-2-ol, 4-amino-3'-methylthio-[1,1'-biphenyl]-2-ol, 4-amino-2'-methylthio-[1,1'-biphenyl]-2-ol, 4-amino-[1,1'-biphenyl]-2,4'-diol, 4-amino-[1,1'-biphenyl]-2,3'-diol, 4-amino-[1,1'-biphenyl]-2,2'-diol, 2,2',3'-trihydroxy-4-amino-[1,1'-biphenyl], 2,2',4'-trihydroxy-4-amino-[1,1'-biphenyl], 2,2',5'-trihydroxy-4-amino-[1,1'-biphenyl], 2,2',6'-trihydroxy-4-amino-[1,1'-biphenyl], 2,3',4'-trihydroxy-4-amino-[1,1'-biphenyl], 2,3',5'-trihydroxy-4-amino-[1,1'-biphenyl], 4-amino-2'-methyl-[1,1'-biphenyl]-2,4'-diol, 2',4-diamino-[1,1'-biphenyl]-2-ol, 3',4-diamino-[1,1'-biphenyl]-2-ol, 4,4'-diamino-[1,1'-biphenyl]-2-ol, 4',4-diamino-[1,1'-biphenyl]-2,2'-diol, 3',4-diamino-[1,1'-biphenyl]-2,2'-ol [sic], 3',4-diamino-[1,1'-biphenyl]-2,4'-ol [sic], 3',4-diamino-[1,1'-biphenyl]-2,5'-ol [sic], 3',4-diamino-[1,1'-biphenyl]-2,6'-ol [sic], 2',3',4-triamino-[1,1'-biphenyl]-2-ol, 2',4,4'-triamino-[1,1'-biphenyl]-2-ol, 2',4,5'-triamino-[1,1'-biphenyl]-2-ol, 2',4,6'-triamino-[1,1'-biphenyl]-2-ol, 3',4,4'-triamino-[1,1'-biphenyl]-2-ol, 3',4,5'-triamino-[1,1'-biphenyl]-2-ol, 1-(4'-amino-2'-hydroxy-1,1'-biphenyl-4-yl)ethanone, 4-amino-1,1':3',1''-terphenyl-2-ol, 4-amino-1,1':4',1''-terphenyl-2-ol, 4-amino-4'-(aminomethyl)-[1,1'-biphenyl]-2-ol, 4-amino-3'-(aminomethyl)-[1,1'-biphenyl]-2-ol, 4-amino-2'-(aminomethyl)-[1,1'-biphenyl]-2-ol, (4'-amino-2'-hydroxy-1,1'-biphenyl-4-yl)acetonitrile, (4'-amino-2'-hydroxy-1,1'-biphenyl-3-yl)acetonitrile, (4'-amino-2'-hydroxy-1,1'-biphenyl-2-yl)acetonitrile, 5-amino-2-(4-pyridinyl)phenol, 5-amino-2-(3-pyridinyl)phenol, 5-amino-2-(2-pyridinyl)phenol, 5-amino-2-(3-methyl-2-pyridinyl)phenol, 5-amino-2-(4-methyl-2-pyridinyl)phenol, 5-amino-2-(5-methyl-2-pyridinyl)phenol, 5-amino-2-(6-methyl-2-pyridinyl)phenol, 5-amino-2-(3-chloro-2-pyridinyl)phenol, 5-amino-2-(4-chloro-2-pyridinyl)phenol, 5-amino-2-(5-chloro-2-pyridinyl)phenol, 5-amino-2-(6-chloro-2-pyridinyl)phenol, 5-amino-2-(3-fluoro-2-pyridinyl)phenol, 5-amino-2-(4-fluoro-2-pyridinyl)phenol, 5-amino-2-(5-fluoro-2-pyridinyl)phenol, 5-amino-2-(6-fluoro-2-pyridinyl)phenol, 5-amino-2-(3-trifluoromethyl-2-pyridinyl)phenol, 5-amino-2-(4-trifluoromethyl-2-pyridinyl)phenol, 5-amino-2-(5-trifluoromethyl-2-pyridinyl)phenol, 5-amino-2-(6-trifluoromethyl-2-pyridinyl)phenol, 5-amino-2-(3-nitro-2-pyridinyl)phenol, 5-amino-2-(4-nitro-2-pyridinyl)phenol, 5-amino-2-(5-nitro-2-pyridinyl)phenol, 5-amino-2-(6-nitro-2-pyridinyl)phenol, 5-amino-2-(2-methyl-3-pyridinyl)phenol, 5-amino-2-(4-methyl-3-pyridinyl)phenol, 5-amino-2-(5-methyl-3-pyridinyl)phenol, 5-amino-2-(6-methyl-3-pyridinyl)phenol, 5-amino-2-(2-chloro-3-pyridinyl)phenol, 5-amino-2-(4-chloro-3-pyridinyl)phenol, 5-amino-2-(5-chloro-3-pyridinyl)phenol, 5-amino-2-(6-chloro-3-pyridinyl)phenol, 5-amino-2-(2-bromo-3-pyridinyl)phenol, 5-amino-2-(4-bromo-3-pyridinyl)phenol, 5-amino-2-(5-bromo-3-pyridinyl)phenol, 5-amino-2-(6-bromo-3-pyridinyl)phenol, 5-amno-2-(2-nitro-3-pyridinyl)phenol, 5-amino-2-(4-nitro-3-pyridinyl)phenol, 5-amino-2-(5-nitro-3-pyridinyl)phenol, 5-amino-2-(6-nitro-3-pyridinyl)phenol, 5-amino-2-(5-pyrimidinyl)phenol and 5-amino-2-(4-pyrimidinyl)phenol, as well as the physiologically compatible, water-soluble salts thereof.

Preferred compounds of formula (I) are those wherein;
(i) R1 stands for a group of formula (II) with R2 and R6 denoting hydrogen, or (ii) R1 stands for a group of formula (E) with $X_1$ and $X_5$ denoting C—R7 and C—R11, with R7 and R11 denoting hydrogen.

Particularly preferred are the following compounds of formula (1):

4-amino-3'-methyl-[1,1'-biphenyl]-2-ol, 4-amino-4'-methyl-3'-nitro-[1,1'-biphenyl]-2-ol, 4-amino-[1,1'-biphenyl]-2,4'-diol, 5-amino-2-(3-pyridinyl)phenol and 5-amino-2-(5-pyrimidinyl)phenol as well as the physiologically compatible, water-soluble salts thereof.

The compounds of formula (I) can be used as the free bases as well as in the form of their physiologically compatible salts of inorganic or organic acids, for example hydrochloric acid, sulfuric acid, phosphoric acid, acetic acid, propionic acid, lactic acid or citric acid.

The 3-aminophenol derivatives of formula (1) are present in the colorant of the invention in a total amount from about 0.005 to 20 weight percent, an amount from about 0.01 to 5 wt. % and particularly from 0.1 to 2.5 weight percent being preferred.

Preferred developers are 1,4-diaminobenzene (p-phenylenediamine), 1,4-diamino-2-methylbenzene (p-toluylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(1-hydroxyethyl)benzene, 1,4-diamino-2-(2-hydroxyethyl)benzene, 1,4-diamino-2-(1-methylethyl)benzene, 1,3-bis-[(4-aminophenyl)(2-hydroxyethyl)amino]-2-propanol, 1,4-bis-[(4-aminophenyl)amino]butane, 1,8-bis-(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol and 1,2,4-trihydroxybenzene.

Moreover, besides the compounds of formula (I) the colorant of the invention can also contain other known couplers, for example N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy) benzene, 1,3-diamino-4-(3-hydroxypropoxy)benzene, 1,3-diamino-4-(2-methoxyethoxy)benzene, 2,4-diamino-1,5-di (2-hydroxyethoxy)-benzene, 1-(2-aminoethoxy)-2,4-diamino benzene, 2-amino-1-(2-hydroxyethoxy)-4-methylaminobenzene, 2,4-diaminophenoxyacetic acid, 3-[di (2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl) aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl) amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

The couplers and developers can be contained in the colorant of the invention either individually or in admixture with each other, the total amount of couplers and developers in the colorant of the invention (based on the total amount of colorant) being from about 0.005 to 20 weight percent, preferably from about 0.01 to 5 weight percent and particularly from 0.1 to 2.5 weight percent, each.

The total amount of the developer-coupler combination contained in the colorant described herein is preferably from about 0.01 to 20 weight percent, an amount from about 0.02 to 10 weight percent and particularly from 0.2 to 6 weight percent being especially preferred. In general, the developers and couplers are used in equimolar amounts. However, it is not disadvantageous if the developers are present in a certain excess or deficiency with respect to such an amount.

Moreover, the colorant of the invention can also contain additional dye components, for example 6-amino-2-methylphenol and 2-amino-5-methylphenol as well as common synthetic or natural direct dyes, for example vegetable dyes or synthetic direct dyes from the group of acid or basic dyes, triphenylmethane dyes, aromatic nitro dyes, azo dyes and disperse dyes. The colorants of the invention can contain these dye components in an amount from about 0.1 to 4 weight percent.

Naturally, the additional couplers and the developers and other dye components, provided they are bases, can also be used in the form of their physiologically compatible salts of organic or inorganic acids, for example hydrochloric acid or sulfuric acid, or—if they contain aromatic OH— groups—in the form of salts of bases, for example as alkali phenoxides.

Moreover, if the colorants are used for dyeing hair, they can also contain common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be formulated, for example, as a solution, particularly an aqueous or aqueous-alcoholic solution. A particularly preferred formulation, however, is a cream, gel or emulsion. Such a preparation consists of a mixture of dye components and additives commonly used for such preparations.

Common additives to solutions, creams, emulsions or gels are, for example, solvents such as water, lower aliphatic alcohols, for example ethanol, propanol or isopropanol, glycerol or glycols such as 1,2-propylene glycol; moreover wetting agents or emulsifiers from the classes of anionic, cationic, amphoteric or nonionic surface-active substances such as, for example, the fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides and ethoxylated fatty esters; furthermore thickeners such as the higher fatty alcohols, starch, cellulose derivatives, petrolatum, paraffin oil and fatty acids; moreover hair-care agents such as cationic resins, lanolin derivatives, cholesterol, pantothenic acid and betaine. The said constituents are used in amounts commonly employed for such purposes, for example the wetting agents and emulsifiers at a concentration from about 0.5 to 30 weight percent, the thickeners in an amount from about 0.1 to 30 weight percent and the hair-care agents at a concentration from about 0.1 to 5 weight percent.

Depending on the composition, the colorant of the invention can be weakly acidic, neutral or alkaline. In particular, it has a pH from 6.5 to 11.5, the adjustment to a basic value preferably being achieved with ammonia. However, amino acids and/or organic amines, for example monoethanolamine or triethanolamine, or inorganic bases, for example sodium hydroxide or potassium hydroxide can also be used.

For pH adjustment in the acidic range, an inorganic or organic acid, for example phosphoric acid, acetic acid, citric acid or tartaric acid, can be used.

For use in oxidative dyeing of hair, the afore-described colorant is mixed with an oxidant just before use and the resulting mixture is applied to the hair in an amount sufficient for the hair treatment, in general in an amount from about 60 to 200 grams, depending on the fullness of the hair.

Suitable oxidants for developing the hair coloration are mainly hydrogen peroxide or the compounds of addition thereof to urea, melamine, sodium borate or sodium carbonate in the form of a 3 to 12%, preferably 6% aqueous solution. Atmospheric oxygen can also be used. If a 6% hydrogen peroxide solution is used as oxidant, the weight ratio of hair colorant to oxidant is from 5:1 to 1:2 and preferably 1:1. Larger amounts of oxidant are used primarily at higher dye concentrations in the hair colorant or when more pronounced hair bleaching is wanted at the same time. The mixture is allowed to act on the hair at 15 to 50° C. for about 10 to 45 minutes, preferably for 30 minutes, after which the hair is rinsed with water and dried. Optionally, following this rinsing the hair is washed with a shampoo and optionally post-rinsed with a weak organic acid, for example citric acid or tartaric acid. The hair is then dried.

The colorant of the invention containing a 3-aminophenol derivative of formula (I) as coupler gives colorations of excellent color stability, particularly in terms of light fastness, wash fastness and rubbing fastness. As far as the coloring properties are concerned, depending on the kind and composition of the dye components, the colorant of the invention provides a wide range of different color shades ranging from blond to brown, purple, violet, blue and black. Said shades are characterized by high color intensity. Furthermore, the very good coloring properties of the colorant of the present patent application are, in particular, characterized by the fact that this colorant also makes it possible to dye gray, chemically not previously damaged hair with good covering power and without any problems.

The aminophenol derivatives of formula (I) of the invention can be prepared by methods of synthesis known from the literature, for example:

a) by tetrakis(triphenylphosphine)palladium(0)-catalyzed coupling of a suitably substituted 3-aminophenolboric acid derivative of formula (IV)

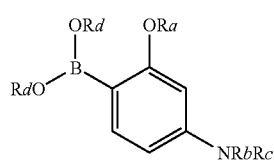

(IV)

with a halogen-substituted compound of formula (IIa) or (IIIa)

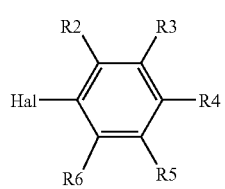

(IIa)

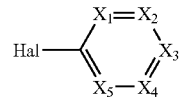

(IIIa)

followed by the removal of the protective group needed for the coupling reaction, or b) by tetrakis(triphenylphosphine)palladium(0)-catalyzed coupling of a halogen-substituted 3-aminophenol derivative of formula (V)

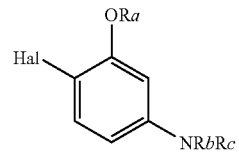

(V)

with a boric acid derivative of formula (IIb) or (IIIb)

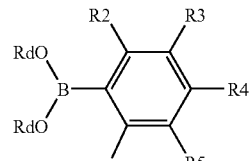

(IIb)

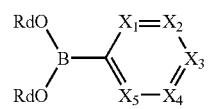

(IIIb)

followed by the removal of the protective group needed for the coupling reaction, the groups in formulas (IIa), (IIb), (IIIa), (IIIb), (IV) and (V) having the following meaning:

Ra denotes a protective group as described, for example, in the chapter on "Protective Groups" in Organic Synthesis, chapter 3, Wiley Interscience, 1991;

Rb and Rc independently of each other denote hydrogen or a protective group as described, for example, in the chapter on "Protective Groups" in Organic Synthesis, chapter 7, Wiley Interscience, 1991;

Rd denotes hydrogen or the two Rd groups together with the —O—B—O— group form an unsubstituted or substituted five-membered or six-membered cycloaliphatic ring;

Hal denotes F, Cl, Br or I; and

R2, R3, R4, R5 and R6 and $X_1$, $X_2$, $X_3$, $X_4$ and $X_5$ have the same meaning as in formulas (II) or (III).

The 3-aminophenol derivatives of formula (I) are readily water-soluble and give colorations of excellent color intensity and color stability, particularly in terms of light fastness, wash fastness and rubbing fastness. Moreover, they have excellent storage stability particularly as constituents of the afore-described oxidative colorants.

Another object of the present invention are novel 3-aminophenol derivatives of the afore-indicated formula (I) or the physiologically compatible, water-soluble salts thereof, provided that (i) R1 is not a 2-pyridyl group and (ii) R1 is not a 2-hydroxy-4-aminophenyl group.

The following examples are intended to illustrate the subject matter of the invention in greater detail without limiting its scope.

EXAMPLES

Examples 1 to 45

Synthesis of 3-aminophenol Derivatives of General Formula (I)

A. Synthesis of 3-ethoxymethoxyphenylamine

A dispersion of 12 g (274.9 mmol) of sodium hydride (55% in oil) was added portionwise at 0° C. to a solution of 20.0 g (183.3 mmol) of 3-aminophenol in 450 mL of dried acetonitrile. The mixture was then allowed to agitate at 0° C. for 3 hours. A solution of 25 g (210.8 mmol) of chloromethyl ethyl ether in 30 mL of acetonitrile was added dropwise, and the mixture was allowed to agitate overnight at room temperature. The reaction mixture was then filtered and the filter cake was washed with a small amount of acetone. The combined filtrates were evaporated. This gave 32.3 g of 3-ethoxymethoxyphenylamine. The resulting crude product was used in the next step without further purification.

$^1$H-NMR (300 MHz, DMSO): δ=6.89 (t, 1H, H5); 6.24 (s, 1H, H2); 6.22 (d, 1H); 6.16 (d, 1H); 5.14 (s, 2H, NH$_2$); 5.11 (s, 2H, OCH$_2$); 3.75 (q, 2H, CH$_2$); 1.13 (t, 3H, CH$_3$).

B. Synthesis of tert butyl N-(3-ethoxymethoxyphenyl)carbamate 30 g (180 mmol) of 3-ethoxymethoxyphenylamine from step A and 44.4 g (203 mmol) of ditert.butyl dicarbonate were dissolved in a mixture of 140 mL of 2N sodium hydroxide and 200 mL of dichloromethane, and the mixture was allowed to agitate for 24 hours at room temperature. The organic phase was then separated, washed to a neutral pH with saturated aqueous sodium chloride solution, dried over MgSO$_4$, filtered and evaporated. The resulting crude product was purified on silica gel using hexane/ethyl acetate (8:1).

This gave 18 g (42% of the theoretical based on the amount of 3-aminophenol used) of tert.butyl N-(3-ethoxymethoxyphenyl)carbamate as a yellow oil.

$^1$H-NMR (300 MHz, DMSO): δ=9.33 (s, 1H, NH); 7.20 (s, 1H, H2); 7.14 (t, J=8.0, 1H, H5); 7.05 (d, J=8.0, 1H, H3); 6.63 (d, J=8.0, 1H, H6); 5.17 (s, 2H, OCH$_2$); 3.64 (q, J=7.1, 2H, CH$_2$); 1.49 (s, 9H, tert.butyl); 1.13 (t, J=7.1, 3H, CH$_3$),

| CHN Analysis (C$_{14}$H$_{21}$NO$_4$) | | | |
|---|---|---|---|
| | % C | % H | % N |
| Calculated | 62.90 | 7.92 | 5.24 |
| Found | 62.60 | 8.04 | 4.97 |

C. Synthesis of tert.butyl N-(4-bromo-3-ethoxymethoxyphenyl)carbamate 13.9 g (52 mmol) of tert.butyl N-(3-ethoxymethoxyphenyl)carbamate from step B and 10.2 g (57.2 mmol) of N-bromosuccinimide were dissolved under nitrogen in 400 ml. of 1,2-dimethoxyethane, and the solution was allowed to agitate for 3 hours at room temperature. The reaction mixture was then poured onto 1000 mL of ice/water and extracted with ethyl acetate. The organic phase was washed with a saturated solution of sodium chloride, dried over magnesium sulfate and filtered and the filtrate was evaporated. The resulting crude product was purified on silica gel using hexane/ethyl acetate (4:1).

This gave 14.4 g (76% of the theoretical) of tert.butyl N-(4-bromo-3-ethoxymethoxyphenyl)carbamate as an oil.

$^1$H-NMR (300 MHz, DMSO): δ=9.50 (s, 1H, NH); 7.45 (d, J=2.0, 1H, H2); 7.43 (d, J=8.6, 1H, H5); 7.04 (dd, J=2.0, J=8.6, 1H, H6); 5.24 (s, 2H, OCH$_2$); 3.70 (q, J=7.1, 2H, CH$_2$); 1.48 (s, 9H, tert.butyl); 1.16 (t, J=7.1, 3H, CH$_3$);

| CHN Analysis (C$_{14}$H$_{20}$BrNO$_4$) | | | |
|---|---|---|---|
| | % C | % H | % N |
| Calculated | 48.57 | 5.82 | 4.05 |
| Found | 47.82 | 5.87 | 3.77 |

D. Synthesis of tert.butyl [4-(5,5-dimethyl-[1,3,2]dioxaborinan-2-yl)-3-ethoxymethoxyphenyl]carbamate 10 g (28.8 mmol) of tert.butyl N-(4-bromo-3-ethoxymethoxyphenyl)carbamate from step C and 13 g (57.6 mmol) of 5,5,5',5'-tetramethyl-2,2'-bi-[1,3,2-dioxaborinane] were dissolved under argon in 260 mL of dioxane. Then, 2.11 g (2.88 mmol) of [1,1'-bis(diphenylphosphino)ferrocene]-dichloropalladium(II) and 8.48 g (86.4 mmol) of potassium acetate were added, and the reaction mixture was heated at 80° C. for 7 hours. The reaction mixture was then poured onto 1.6 L of ice/water and extracted with ethyl acetate. The organic phase was washed with saturated aqueous sodium chloride solution, dried over magnesium sulfate and filtered and the filtrate was evaporated. The resulting crude product was purified on silica gel using hexane/ethyl acetate (2:1).

This gave 5.84 g (54% of the theoretical) of tert.butyl [4-(5,5-dimethyl-[1,3,2]dioxaborinan-2-yl)-3-ethoxymethoxyphenyl]carbamate.

1H-NMR (300 MHz, DMSO): δ=9.40 (s, 1H, NH); 7.41 (d, J=8.1, 1H, H5); 7.21 (s, 1H, H2); 7.07 (d, J=8.1, 1H, H6); 5.09 (s, 2H, OCH$_2$); 3.69 (s, 4H, BOCH$_2$); 3.66 (q, J=7.1, 2H, CH$_2$); 1.48 (s, 9H, tert.butyl); 1.18 (t, 3H, CH$_3$); 0.95 (s, 6H, CH$_3$).

E. Synthesis of the 3-aminophenols of Formula (1)

0.23 g (0.6 mmol) of tert.butyl [4-(5,5-dimethyl-[1,3,2] dioxaborinan-2-yl)-3-ethoxymethoxyphenyl]carbamate from step D and 0.78 mmol of the appropriate bromo derivative were dissolved under argon in 4 mL of 1,2-dimethoxyethane. Then, 0.07 g (0.06 mmol) of tetrakis (triphenylphosphine)palladium and 0.8 mL of 2N potassium carbonate solution were added, and the reaction mixture was heated at 80° C. At the end of the reaction, the reaction mixture was poured into 15 mL of ethyl acetate, and the organic phase was extracted with 1N sodium hydroxide solution and then dried with magnesium sulfate. The solvent was distilled off in a rotary evaporator, and the residue was purified on silica gel using hexane/ethyl acetate.

The product thus obtained was dissolved in 2 mL of ethanol and to it was added 1 mL of a 2.9 molar solution of ethanolic hydrochloric acid or of 4-molar hydrochloric acid in dioxane. The reaction mixture was then heated at 55° C. At the end of the reaction, the precipitate was filtered off, washed with ethanol (or dioxane) and then dried.

1. 4-Amino-[1,1'-biphenyl]-2-ol hydrochloride
   Bromo derivative used: bromobenzene
   Yield: 0.041 g (31% of the theoretical)
   ESI-MS: 186 [M+H]$^+$ (100)

2. 4-Amino-4'-methyl-[1'-biphenyl]-?-ol hydrochloride
   Bromo derivative used: 4-bromotoluene
   Yield: 0.026 g (18% of the theoretical)
   ESI-MS: 200 [M+H]$^+$ (100)

3. 4-Amino-3'-methyl-[1,1'-biphenyl]-2-ol hydrochloride
   Bromo derivative used: 3-bromotoluene
   Yield: 0.048 g (28% of the theoretical)
   ESI-MS: 200 [M+H]$^+$ (100)
   $^1$-NMR (300 MHz, DMSO): δ=10.15 (s, 1H, OH); 7.31 (s, 1H, H2'); 7.29 (m, 3H); 7.13 (d, J=8.1, 1H, H6'); 7.00 (d, J=1.7, 1H, H3); 6.83 (dd, J=1.7, J=8.1, 1H, H5); 3.60 (s, br, 3H, NH$_3^+$); 2.35 (s, 3H, CH$_3$).

4. 4-Amino-2',3'-dimethyl-[1,1'-biphenyl]-2-ol hydrochloride
   Bromo derivative used: 3-bromo-o-xylene
   Yield: 0.046 g (32% of the theoretical)
   ESI-MS: 214 [M+H]$^+$ (100)

5. 4-Amino-2',5'-dimethyl-[1,1'-biphenyl]-2-ol hydrochloride
   Bromo derivative used: 2-bromo-p-xylene
   Yield: 0.046 g (32% of the theoretical)
   ESI-MS: 214 [M+H]$^+$ (100)

6. 4-Amino-2',4'-dimethyl-[1,1'-biphenyl]-ol hydrochloride
   Bromo derivative used: 6-bromo-m-xylene
   Yield: 0.033 g (17% of the theoretical)
   ESI-MS: 214 [M+H]$^+$ (100)

7. 4-Amino-3',4'-dimethyl-[1,1'-biphenyl]-2-ol hydrochloride
   Bromo derivative used: 4-bromo-o-xylene
   Yield: 0.048 g (32% of the theoretical)
   ESI-MS: 214 [M+H]$^+$ (100)

8. 4-Amino-3',5'-dimethyl-[1,1'-biphenyl]-2-ol hydrochloride
   Bromo derivative used: 5-bromo-m-xylene
   Yield: 0.021 g (13% of the theoretical)
   ESI-MS: 214 [M+H]$^+$ (100)

9. 4-Amino-2',4',5'-trimethyl-[1,1'-biphenyl]-2-ol hydrochloride
   Bromo derivative used: 5-bromo-1,2,4-trimethylbenzene
   Yield: 0.023 g (14% of the theoretical)
   ESI-MS: 228 [M+H]$^+$ (100)

10. 4-Amino-4'-chloro-[1,1'-biphenyl]-2-ol hydrochloride,
    Bromo derivative used: 1-bromo-4-chlorobenzene
    Yield: 0.016 g (10% of the theoretical)
    ESI-MS: 220 [M+H]$^+$ (100)

11. 4-Amino-4'-chloro-[1'-biphenyl]-2-ol hydrochloride
    Bromo derivative used: 1-bromo-3-chlorobenzene
    Yield: 0.036 g (23% of the theoretical)
    ESI-MS: 220 [M+H]$^+$ (100)

12. 4-Amino-2'-chloro-[1,1'-biphenyl]-2-ol hydrochloride
    Bromo derivative used: 1-bromo-2-chlorobenzene
    Yield: 0.018 g (12% of the theoretical)
    ESI-MS: 220 [M+H]$^+$ (100)

13. 4-Amino-3',5'-dichloro-[1,1'-biphenyl]-2-ol hydrochloride
    Bromo derivative used: 1-bromo-3,5-dichlorobenzene
    Yield: 0.074 g (40% of the theoretical)
    ESI-MS: 254 [M+H]$^+$ (100)

14. 4-Amino-4'-fluoro-[1,1'-biphenyl]-2-ol hydrochloride
    Bromo derivative used: 1-bromo-4-fluorobenzene
    Yield: 0.047 g (33% of the theoretical)
    ESI-MS: 204 [M+H]$^+$ (100)

15. 4-Amino-3',5'-difluoro-[1,1'-biphenyl]-2-ol hydrochloride
    Bromo derivative used: 1-bromo-4-fluorobenzene
    Yield: 0.024 g (16% of the theoretical)
    ESI-MS: 220 [M–H]$^+$ (100)

16. 4-Amino-3'-bromo-5'-methyl-[1,1'-biphenyl]-2-ol hydrochloride
    Bromo derivative used: 3,5-dibromotoluene
    Yield: 0.022 g (12% of the theoretical)
    ESI-MS: 278 [M]$^+$ (100)

17. 4-Amino-4'-(trifluoromethyl)-[1,1'-biphenyl]2-ol hydrochloride
    Bromo derivative used: 1-bromo-4-(trifluoromethyl)benzene
    Yield: 0.017 g (10% of the theoretical)
    ESI-MS: 254 [M+H]$^+$ (100)

18. 4-Amino-3'-(trifluoromethyl)-[1,1'-biphenyl]-2-ol hydrochloride
    Bromo derivative used: 1-bromo-4-(trifluoromethyl)benzene
    Yield: 0.017 g (10% of the theoretical)
    ESI-MS: 254 [M+H]$^+$ (100)

19. 4-Amino-1'-nitro-[1,1'-biphenyl]-2-ol hydrochloride
    Bromo derivative used: 1-bromo-3-nitrobenzene
    Yield: 0.029 g (18% of the theoretical)
    ESI-MS: 253 [M+Na]$^+$ (100)
    $^1$H-NMR (300 MHz, DMSO): δ=10.40 (s, br, 1H, OH); 8.16 (d, J=8.0, 1H, H4'); 8.00 (d, J=8.0, 1H, H6'); 7.72 (dd, J=8.0, J=8.0, 1H, H5'); 7.43 (d, J=8.2, 1H, H6); 6.92 (s, 1H, H3); 6.78 (d, J=8.2, 1H, H5); 3.46 (s, br, 3H, NH$_3^+$).

20. 4-Amino-4'-methyl-3'-nitro-[1,1'-biphenyl]-2-ol hydrochloride
    Bromo derivative used: 1-bromo-2-nitrotoluene
    Yield: 0.082 g (49% of the theoretical)
    ESI-MS: 267 [M+Na]$^+$ (100)
    $^1$H-NMR (300 MHz, DMSO): δ=10.39 (s, br, 1H, OH); 8.16 (d, J=1.7, 1H, H2'); 7.81 (dd, J=1.7, J=8.0, 1H, H6'); 7.54, (d, J=8.0, 1H, H5'); 7.41 (d, J=8.2, 1H, H6); 6.98 (d, J=1.8, 1H, H3); 6.82 (dd, J=1.8, J=8.1, 1H, H5); 3.46 (s, br, 3H, NH$_3^+$); 2.54 (s, 3H, CH$_3$).

| CHN Analysis: (C$_{13}$H$_{13}$N$_2$O$_3$HCl) | | | | |
|---|---|---|---|---|
| | % C | % H | % N | % Cl |
| Calculated | 55.62 | 4.67 | 9.98 | 12.63 |
| Found: | 55.10 | 4.60 | 9.50 | 12.20 |

21. 4-Amino-2'-nitro-4'-(trifluoromethyl)[1,1'-biphenyl-2-ol hydrochloride
    Bromo derivative used: 1-bromo-2-nitro-4-(trifluoromethyl)benzene
    Yield: 0.057 g (28% of the theoretical)
    ESI-MS: 297 [M–H]$^+$ (100)

22. 4'-Amino-2'-hydroxy-[1,1'-biphenyl]-1-carbonitrile hydrochloride
   Bromo derivative used: 3-bromobenzonitrile
   Yield: 0.036 g (24% of the theoretical)
   ESI-MS: 233 [M+Na]$^+$ (100)

23. 4-Amino-4'-methoxy-[1,1'-biphenyl]-2-ol hydrochloride
   Bromo derivative used: 1-bromo-4-methoxybenzene
   Yield: 0.021 g (14% of the theoretical)
   ESI-MS: 216 [M+H]$^+$ (100)

24. 4-Amino-3'-methoxy-[1,1'-biphenyl]-2-ol hydrochloride
   Bromo derivative used: 1-bromo-3-methoxybenzene
   Yield: 0.01 g (7% of the theoretical)
   ESI-MS: 216 [M+H]$^+$ (100)

25. 4-Amino-2'-methoxy-[1,1'-biphenyl]-2-ol hydrochloride
   Bromo derivative used: 1-bromo-2-methoxybenzene
   Yield: 0.058 g (36% of the theoretical)
   ESI-MS: 214 [M–H]$^+$ (100)

26. 4-Amino-4'-ethoxy-[1,1'-biphenyl]-2-ol hydrochloride
   Bromo derivative used: 1-bromo-4-ethoxybenzene
   Yield: 0.020 g (13% of the theoretical)
   ESI-MS: 230 [M+H]$^+$ (100)

27. 4-Amino-2',4'-dimethoxy-[1,1'-biphenyl]-2-ol hydrochloride
   Bromo derivative used: 1-bromo-2,4-dimethoxybenzene
   Yield: 0.050 g (30% of the theoretical)
   ESI-MS: 268 [M+Na]$^+$ (100)

28. 4-Amino-2',5'-dimethoxy-[1,1']-2-biphenyl]-2-ol hydrochloride
   Bromo derivative used: 2-bromo-1,4-dimethoxybenzene
   Yield: 0.061 g (36% of the theoretical)
   ESI-MS: 268 [M+Na]$^+$ (100)

29. 5-Amino-2-(1,3-benzodioxo-5-yl)phenol hydrochloride
   Bromo derivative used: 5-bromo-1,3-benzodioxol
   Yield: 0.030 g (19% of the theoretical)
   ESI-MS: 230 [M+H]$^+$ (100)
   $^1$H-NMR (300 MHz DMSO): δ=10.10 (s, br, 1H, OH)); 7.28 (d, J=8.2, 1H, H3); 7.09 (s, 1H, H4'); 6.96 (m, 2H, H6' and H7'); 6.91 (s, 1H, H6); 6.77 (d, J=8.2, 1H, H4); 6.04 (s, 2H, CH$_2$O); 3.50 (s, br, 3H, NH$_3^+$).

30. 4-Amino-4'-methoxy-2'-methyl-[1,1'-biphenyl]-2-ol hydrochloride
   Bromo derivative used: 1-bromo-4-methoxy-2-methylbenzene
   Yield: 0.016 g (10% of the theoretical)
   ESI-MS: 230 [M+H]$^+$ (100)

31. 4-Amino-4'-phenoxy-[1,1'-biphenyl]-2-ol hydrochloride
   Bromo derivative used: 1-bromo-4-phenoxybenzene
   Yield: 0.024 g (13% of the theoretical)
   ESI-MS: 276 [M–H]$^+$ (100)

32. 4-Amino-[1,1'-biphenyl]-2,4'-diol hydrochloride
   Bromo derivative used: 4-bromophenol
   Yield: 0.033 g (23% of the theoretical)
   ESI-MS: 200 [M–H]$^+$ (100)

33. 4-Amino-2'-methyl-[1,1'-biphenyl]-2,4'-diol hydrochloride
   Bromo derivative used: 4-bromo-3-methylphenol
   Yield: 0.012 g (8% of the theoretical)
   ESI-MS: 216 [M+H]$^+$ (100)

34. 3',4-Diamino-[1,1'-biphenyl]-2-ol hydrochloride
   Bromo derivative used: 3-bromoaniline
   Yield: 0.032 g (23% of the theoretical)
   ESI-MS: 199 [M–H]$^+$ (100)

35. 1-(4'-Amino-2'-hydroxy-1,1'-biphenyl-4-yl)ethanone hydrochloride
   Bromo derivative used: 4-bromoacetophenone
   Yield: 0.016 g (10% of the theoretical)
   ESI-MS: 250 [M+Na]$^+$ (100)

36. 4-Amino-1,1':3',1''-terphenyl-2-ol hydrochloride
   Bromo derivative used: 3-bromo-1,1'-biphenyl
   Yield: 0.050 g (28% of the theoretical)
   ESI-MS: 260 [M–H]$^+$ (100)

37. 5-Amino-2-(3-pyridinyl)phenol hydrochloride
   Bromo derivative used: 3-bromopyridine
   Yield: 0.067 g (50% of the theoretical)
   ESI-MS: 187 [M+H]$^+$ (100)
   $^1$H-NMR (300 MHz, DMSO): δ=10.88 (s, br, 1H, OH); 9.09 (s, 1H, H2'); 8.81 (d, J=5.5, 1H, H4'); 8.76 (d, J=8.2, 1H, H6'); 8.09 (dd, J=5.5, J=8.2, 1H, H5'); 7.54 (d, J=8.3, 1H, H3); 7.02 (d, J=1.7, 1H, H6); 6.84 (dd, J=1.7, J=8.3, 1H, H4); 4.2 (s, br, 3H, NH$_3^+$).

38. 5-Amino-2-(2-pyridinyl)phenol hydrochloride
   Bromo derivative used: 2-bromopyridine
   Yield: 0.038 g (28% of the theoretical)
   ESI-MS: 187 [M+H]$^+$ (100)

39. 5-Amino-2-(3-methyl-2-pyridinyl)phenol hydrochloride
   Bromo derivative used: 2-bromo-3-methylpyridine
   Yield: 0.039 g (27% of the theoretical)
   ESI-MS: 201 [M+H]$^+$ (100)

40. 5-Amino-2-(4-methyl-2-pyridinyl)phenol hydrochloride
   Bromo derivative used: 2-bromo-4-methylpyridine
   Yield: 0.057 g (39% of the theoretical)
   ESI-MS: 201 [M+H]$^+$ (100)

41. 5-Amino-2-(5-methyl-2-pyridinyl)phenol hydrochloride
   Bromo derivative used: 2-bromo-5-methylpyridine
   Yield: 0.051 g (35% of the theoretical)
   ESI-MS: 201 [M+H]$^+$ (100)

42. 5-Amino-2-(6-methyl-2-pyridinyl)phenol hydrochloride
   Bromo derivative used: 2-bromo-6-methylpyridine
   Yield: 0.056 g (39% of the theoretical)
   ESI-MS: 201 [M+H]$^+$ (100)

43. 5-Amino-2-(5-nitro-2-pyridinyl)phenol hydrochloride
   Bromo derivative used: 2-bromo-5-nitropyridine
   Yield: 0.060 g (37% of the theoretical)
   ESI-MS: 230 [M–H]$^+$ (100)

44. 5-Amino-2-(5-bromo-3-pyridinyl)phenyl hydrochloride
   Bromo derivative used: 3,5-dibromopyridine
   Yield: 0.047 g (26% of the theoretical)
   ESI-MS: 265 [M]$^+$ (100)
   $^1$H-NMR (300 MHz, DMSO): δ=10.54 (s, br, 1H, OH); 8.75 (s, 1H, H2'); 8.67 (s, 1H, H6'); 8.24 (s, 1H, H4'); 7.54 (d, J=8.2, 1H, H3); 6.97 (s, 1H, H6); 6.82 (d, J=8.2 1H, H4).

45. 5-Amino-2-(5-pyrimidinyl)phenol hydrochloride
   Bromo derivative used: 5-bromopyrimidine
   Yield: 0.067 g (50% of the theoretical)
   ESI-MS: 188 [M+H]$^+$ (100)
   $^1$H-NMR (300 MHz, DMSO): δ=10.74 (s, br, 1H, OH); 9.14 (s, 1H, H2'); 9.00 (s, 2H, H4' and H6'); 7.52 (d, J=8.1, 1H, H3); 7.10 (d, J=1.6, 1H, H6); 6.93 (dd, J=1.6, J=8.1, 1H, H4); 3.76 (s, br, 3H, NH$_3^+$).

Examples 46 to 90

Hair Colorants

Hair colorant solutions of the following composition were prepared:

| | |
|---|---|
| 1.25 mmol | of the substance of formula (I) as per Table 1 |
| 1.25 mmol | of the developer as per Table 1 |
| 10.0 g | of lauryl ether sulfate (28% aqueous solution) |
| 9.0 g | of ammonia (22% aqueous solution) |
| 7.8 g | of ethanol |
| 0.3 g | of ascorbic acid |
| 0.3 g | of disodium ethylenediaminetetraacetate hydrate |
| to 100.0 g | water, demineralized |

Just before use, 10 g of the above colorant solution was mixed with 10 g of a 6% hydrogen peroxide solution. The mixture was then applied to bleached hair. After an exposure time of 30 minutes at 40° C., the hair was rinsed with water, washed with a commercial shampoo and dried. Table 1 summarizes the resulting colorations.

| | | Developer | | | |
|---|---|---|---|---|---|
| Example | Coupler of Formula (I) | I 2,5-diamino-toluene sulfate | II 2,5-diamino-phenylethanol sulfate | III 4,5-diamino-1-(2'-hydroxy-ethyl)pyrazole sulfate | IV 4-amino-3-methyl-phenol |
| 46 | as per Example 1 | violet | violet | purple | light pink |
| 47 | as per Example 2 | violet | violet | purple | light pink |
| 48 | as per Example 3 | dark-violet | dark-violet | purple | light pink |
| 49 | as per Example 4 | ash-blond | ash-blond | bright red | beige |
| 50 | as per Example 5 | light gray-violet | light gray-violet | bright red | beige |
| 51 | as per Example 6 | violet | violet | bright red | beige |
| 52 | as per Example 7 | violet | violet | bright red | light pink |
| 53 | as per Example 8 | violet | violet | purple | light pink |
| 54 | as per Example 9 | gray | gray | bright red | beige |
| 55 | as per Example 10 | violet | violet | purple | light pink |
| 56 | as per Example 11 | violet | violet | purple | light pink |
| 57 | as per Example 12 | gray-violet | gray-violet | purple | beige |
| 58 | as per Example 13 | gray-violet | gray-violet | bright red | beige |
| 59 | as per Example 14 | violet | violet | bright red | beige |
| 60 | as per Example 15 | blue-violet | blue-violet | strawberry red | light pink |
| 61 | as per Example 16 | light-violet | light-violet | bright red | beige |
| 62 | as per Example 16 | light violet | light violet | bright red | beige |
| 63 | as per Example 18 | bluish violet | bluish violet | strawberry red | light pink |
| 64 | as per Example 19 | dark-blue violet | dark-blue violet | strawberry red | light pink |
| 65 | as per Example 20 | dark-blue violet | dark-blue violet | strawberry red | light pink |
| 66 | as per Example 21 | ash-blond | ash-blond | bright red | beige |
| 67 | as per Example 22 | bluish violet | bluish violet | strawberry red | light pink |
| 68 | as per Example 23 | violet | violet | bright red | beige |
| 69 | as per Example 24 | dark violet | dark violet | purple | light pink |
| 70 | as per Example 25 | violet | violet | bright red | beige |
| 71 | as per Example 26 | light-violet | light-violet | bright | beige |

-continued

| Example | Coupler of Formula (I) | Developer I 2,5-diamino-toluene sulfate | Developer II 2,5-diamino-phenylethanol sulfate | Developer III 4,5-diamino-1-(2'-hydroxy-ethyl)pyrazole sulfate | Developer IV 4-amino-3-methyl-phenol |
|---|---|---|---|---|---|
| 72 | as per Example 27 | light gray-violet | light gray-violet | bright red | beige |
| 73 | as per Example 28 | ash-blond | ash-blond | bright red | beige |
| 74 | as per Example 29 | violet | violet | purple | light pink |
| 75 | as per Example 30 | light violet | light violet | bright red | beige |
| 76 | as per Example 31 | light-violet | light-violet | bright red | beige |
| 77 | as per Example 32 | dark-violet | dark-violet | purple | light pink |
| 78 | as per Example 33 | light-violet | light-violet | bright red | beige |
| 79 | as per Example 34 | dark violet | dark violet | purple | light pink |
| 80 | as per Example 35 | light-blue violet | light-blue violet | light-strawberry red | light pink |
| 81 | as per Example 36 | light-violet | light-violet | bright red | beige |
| 82 | as per Example 37 | dark blue | dark blue | strawberry red | beige pink |
| 83 | as per Example 38 | ash-blond | ash-blond | bright red | beige |
| 84 | as per Example 39 | ash-blond | ash-blond | bright red | beige |
| 85 | as per Example 40 | ash-blond | ash-blond | bright red | beige |
| 86 | as per Example 41 | gray | gray | bright red | beige |
| 87 | as per Example 42 | gray | gray | bright red | beige |
| 88 | as per Example 43 | light-blond | light-blond | bright red | yellow |
| 89 | as per Example 44 | dark blue | dark blue | strawberry red | light pink |
| 90 | as per Example 45 | dark blue | dark blue | strawberry red | light pink |

Examples 91 to 114

Hair Colorants

Hair colorant solutions of the following composition were prepared:

| | |
|---|---|
| X g | of 3-aminophenol derivative of formula (I) (coupler K1 to K4 as per Table 4) |
| U g | of developer E8 to E15 as per Table 2 |
| Y g | of coupler K12 to K36 as per Table 4 |
| 10.0 g | of lauryl ether sulfate (28% aqueous solution) |
| 9.0 g | of ammonia (22% aqueous solution) |
| 7.8 g | of ethanol |
| 0.3 g | of ascorbic acid |
| 0.3 g | of disodium ethylenediaminetetraacetate hydrate |
| to 100.0 g | water, demineralized |

Just before use, 30 g of the above colorant solution was mixed with 30 g of a 6% aqueous hydrogen peroxide solution. The mixture was then applied to bleached hair. After an exposure time of 30 minutes at 40° C., the hair was rinsed with water, washed with a commercial shampoo and dried. Table 5 summarizes the resulting colorations.

TABLE 2

| | Developers |
|---|---|
| E8 | 1,4-diaminobenzene |
| E9 | 2,5-diaminophenylethanol sulfate |
| E10 | 3-methyl-4-aminophenol |
| E11 | 4-amino-2-aminomethylphenol dihydrochloride |
| E13 | N,N-bis-(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

| | Direct Dyes |
|---|---|
| D2 | 6-chloro-2-ethylamino-4-nitrophenol |
| D3 | 2-amino-6-chloro-4-nitrophenol |

TABLE 4

| | Couplers |
|---|---|
| K1 | 4-amino-3'-methyl-[1,1'-biphenyl]-2-ol |
| K2 | 4-amino-4'-methyl-3'-nitro-[1,1'-biphenyl]-2-ol |
| K3 | 5-amino-2-(3-pyridinyl)phenol |
| K4 | 5-amino-2-(5-pyrimidinyl)phenol |

TABLE 4-continued

| | Couplers |
|---|---|
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K18 | N-(3-dimethylamino)phenylurea |
| K19 | 1,3-bis-(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxy-benzene hydrochloride |
| K36 | 2-amino-5-methylphenol |

TABLE 5

Hair Colorants

| | Example No. | | | | | |
|---|---|---|---|---|---|---|
| | 91 | 92 | 93 | 94 | 95 | 96 |
| Dyes | (Dye quantity in grams) | | | | | |
| K1 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

| | Example No. | | | | | |
|---|---|---|---|---|---|---|
| | 97 | 98 | 99 | 100 | 101 | 102 |
| Dyes | (Dye quantity in grams) | | | | | |
| K2 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

| | Example No. | | | | | |
|---|---|---|---|---|---|---|
| | 103 | 104 | 105 | 106 | 107 | 108 |
| Dyes | (Dye quantity in grams) | | | | | |
| K3 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |

TABLE 5-continued

Hair Colorants

| | | | | | | |
|---|---|---|---|---|---|---|
| K12 | | 0.05 | | | | |
| K13 | | | 0.05 | | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

| | Example No. | | | | | |
|---|---|---|---|---|---|---|
| | 109 | 110 | 111 | 112 | 113 | 114 |
| Dyes | (Dye quantity in grams) | | | | | |
| K4 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

Examples 115 to 138

Hair Colorants

Hair colorant solutions of the following composition were prepared:

| X g | of 3-aminophenol derivative of formula (I) (coupler K1 to K4 as per Table 4) |
|---|---|
| U g | of developer E8 to E15 as per Table 2 |
| Y g | of coupler K11 to K36 as per Table 4 |
| Z g | of direct dye D2 and/or D3 as per Table 3 |
| 10.0 g | of lauryl ether sulfate (28% aqueous solution) |
| 9.0 g | of ammonia (22% aqueous solution) |
| 7.8 g | of ethanol |
| 0.3 g | of ascorbic acid |
| 0.3 g | of disodium ethylenediaminetetraacetate hydrate |
| to 100.0 g | water, demineralized |

Just before use, 30 g of the above colorant cream was mixed with 30 g of a 6% aqueous hydrogen peroxide solution. The mixture was then applied to hair. After an exposure time of 30 minutes at 40° C., the hair was rinsed with water, washed with a commercial shampoo and dried. Table 6 summarizes the resulting colorations.

TABLE 6

Hair Colorants

| Dyes | Example No. 115 | 116 | 117 | 118 | 119 | 120 |
|---|---|---|---|---|---|---|
| | (Dye quantity in grams) | | | | | |
| K1 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K19 | 0.10 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 0.05 |
| Coloring result | black | black | black | brown | brown | brown |

| Dyes | Example No. 121 | 122 | 123 | 124 | 125 | 126 |
|---|---|---|---|---|---|---|
| | (Dye quantity in grams) | | | | | |
| K2 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 0.05 |
| Coloring result | black | black | black | brown | brown | brown |

| Dyes | Example No. 127 | 128 | 129 | 130 | 131 | 132 |
|---|---|---|---|---|---|---|
| | (Dye quantity in grams) | | | | | |
| K3 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 005 |
| Coloring result | black | black | black | brown | brown | brown |

| Dyes | Example No. 133 | 134 | 135 | 136 | 137 | 138 |
|---|---|---|---|---|---|---|
| | (Dye quantity in grams) | | | | | |
| K4 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 0.05 |
| Coloring result | black | black | black | brown | brown | brown |

Unless otherwise indicated, the percentages given in the present patent application are by weight.

The invention claimed is:

1. Agent for dyeing keratin fibers based on a developer-coupler combination and characterized in that it contains at least one 3-aminophenol derivative of formula (I) or a physiologically compatible, water-soluble salt thereof

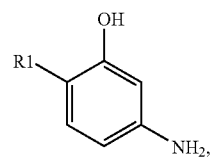
(I)

wherein R1 denotes a group of formula (II) or (III)

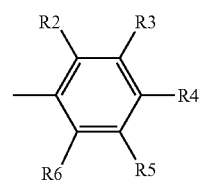
(II)

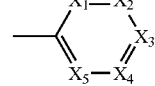
(III)

wherein R2, R3, R4, R5 and R6 independently of each other denote hydrogen, a halogen atom, a cyano group, hydroxyl group, $(C_1-C_4)$-alkoxy group, a phenoxy group, a $(C_1-C_4)$-hydroxyalkoxy group, a $(C_1-C_6)$-alkyl group, a phenyl group, a $(C_1-C_4)$-alkyl thioether group, a mercapto group, a nitro group, an amino group, a $(C_1-C_4)$-alkylamino group, a hydroxy$(C_2-C_4)$alkylamino group, a di$(C_1-C_4)$alkylamino group, a di[hydroxy$(C_2-C_4)$alkyl]amino group, a [dihydroxy $(C_3-C_4)$alkyl]-amino group, a [hydroxy$(C_2-C_4)$ alkyl]-$(C_1-C_4)$-alkylamino group, a trifluoromethyl group, a —C(O)H group, a —C(O)CH$_3$ group, a —C(O)CF$_3$ group, a —Si(CH$_3$)$_3$ group, a $(C_1-C_4)$-hydroxyalkyl group, a $(C_2-C_4)$-dihydroxyalkyl group, a $(C_1-C_4)$-ami-noalkyl group or a $(C_1-C_4)$-cyanoalkylgroup, or two adjacent R2 to R6 groups form an —O—CH$_2$—O-bridge;

$X_1$, $X_2$, $X_3$, $X_4$ and $X_5$ independently of each other denote nitrogen or a C—R7 group, C—R8 group, C—R9 group, C—R10 group or C—R11 group, provided that at least one and at the most three of the $X_1$ to $X_5$ groups denote nitrogen; and R7, R8, R9, R10 and R11 independently of each other denote hydrogen, a halogen atom, a cyano group, a $(C_1-C_6)$-alkyl group, a $(C_1-C_4)$-alkyl thioether group, a mercapto group, a nitro group, an amino group a $(C_1-C_4)$-alkylamino group, a di$(C_1-C_4)$alkylamino group, a trifluoromethyl group, a —C(O)H group, a —C(O)CH$_3$ group, a —C(O)CF$_3$ group, a —Si(CH$_3$)$_3$ group, a —C(O)—NH$_2$ group, a $(C_1-C_4)$-hydroxyalkyl group or a $(C_2-C_4)$-dihydroxyalkyl group.

2. Agent according to claim 1, characterized in that for the compounds of formula (I) (i) R1 stands for a group of formula (II) with R2 and R6 denoting hydrogen, or (ii) R1 stands for a group of formula (I) with $X_1$ and $X_5$ denoting C—R7 and C—R11, with R7 and R11 denoting hydrogen.

3. Agent according to claim 1 or 2, characterized in that the compounds of formula (I) are selected from among 4-amino-3'-methyl-[1,1'-biphenyl]-2-ol, 4-amino-4'-methyl-3'-nitro-[1,1'-biphenyl]-2-ol, 4-amino-[1,1'-biphenyl]-2,4'-diol, 5-amino-2-(3-pyridinyl)phenol and 5-amino-2-(5-pyrimidinyl)phenol as well as the physiologically compatible, water-soluble salts thereof.

4. Agent according to one of claims 1 to 3, characterized in that it contains the 3-aminophenol derivative of formula (I) in an amount from 0.005 to 20 weight percent.

5. Agent according to one of claims 1 to 4, characterized in that the developer is selected from the group consisting of 1,4-diaminobenzene, 1,4-diamino-2-methylbenzene, 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino]aniline, 4-[di(2-hydroxyethyl)amino]-2-methylaniline, 4-[(2-methoxy-ethyl)amino]aniline, 4-[(3-hydroxypropyl)amino]aniline, 4-[(2,3-dihydroxypropyl)amino]aniline, 1,4-diamino-2-(1-hydroxyethyl)benzene, 1,4-diamino-2-(2-hydroxyethyl)benzene, 1,4-diamino-2-(1-methylethyl)benzene, 1,3-bis-[(4-aminophenyl)(2-hydroxyethyl)amino]-2-propanol, 1,4-bis-[(4-aminophenyl)amino]butane, 1,8-bis-(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluoro-phenol, 4-amino-2-[(2-hydroxyethyl)amino]-methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol and 1,2,4-trihydroxybenzene.

6. Agent according to one of claims 1 to 5, characterized in that besides the compounds of formula (I) it contains at least one additional known coupler selected from the group consisting of N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 1,3-diamino-4-(3-hydroxypropoxy)benzene, 1,3-diamino-4-(2-methoxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxy-2-ethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophen o3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)-amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

7. Agent according to one of claims 1 to 6, characterized in that, based on the total amount of colorant, it contains the developers and couplers in a total amount of 0.005 to 20 weight percent, each.

8. Agent according to one of claims 1 to 7, characterized in that it contains additionally at least one direct dye.

9. Agent according to one of claims 1 to 8, characterized in that it has a pH from 6.5 to 11.5.

10. Ready-to-use agent for oxidative dyeing of keratin fibers which, in a medium appropriate for dyeing, contains at least one developer, at least one coupler and at least one oxidant, characterized in that it contains as the coupler at least one 3-aminophenol derivative of formula (I) according to one of claims 1 to 3.

11. Agent according to one of claims 1 to 10, characterized in that it is a hair colorant.

12. 3-Aminophenol derivative of formula (I) or a physiologically compatible, water-soluble salt thereof

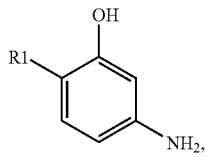
(I)

wherein R1 denotes a group of formula (II) or (III)

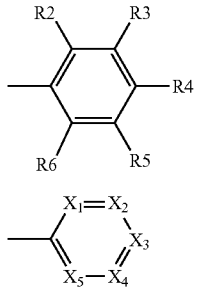
(II)

(III)

wherein R2, R3, R4, R5 and R6 independently of each other denote hydrogen, a halogen atom, a cyano group, hydroxyl group, $(C_1-C_4)$-alkoxy group, a phenoxy group, a $(C_1-C_4)$-hydroxyalkoxy group, a $(C_1-C_6)$-alkyl group, a phenyl group, a $(C_1-C_4)$-alkyl thioether group, a mercapto group, a nitro group, an amino group, a $(C_1-C_4)$-alkylaMino group, a hydroxy-$(C_2-C_4)$-alkylamino group, a di$(C_1-C_4)$-alkylamino group, a di[hydroxy-$(C_2-C_4)$-alkyl]amino group, a [dihydroxy-$(C_3-C_4)$alkyl]amino group, a [hydroxy-$(C_2-C_4)$-alkyl]-$(C_1-C_4)$-alkylamino group, a trifluoromethyl group, a —C(O)H group, a —C(O)CH$_3$ group, a —C(O)CF$_3$ group, a —Si(CH$_3$)$_3$ group, a $(C_1-C_4)$-hydroxyalkyl group, a $(C_2-C_4)$-dihydroxyalkyl group, a $(C_1-C_4)$-aminoalkyl group or a $(C_1-C_4)$-cyanoalkylgroup, or two adjacent R2 to R6 groups form an —O—CH$_2$—O— bridge;

$X_1$, $X_2$, $X_3$, $X_4$ and $X_5$ independently of each other denote nitrogen of a C—R7 group, C—R8 group, C—R9 group, C—R10 group or C—R11 group, provided that at least one and at the most three of the $X_1$ to $X_5$ groups denote nitrogen; and R7, R8, R9, R10 and R11 independently of each other denote hydrogen, a halogen atom, a cyano group, a $(C_1-C_6)$-alkyl group, a $(C_1-C_4)$-alkyl thioether group, a mercapto group, a nitro group, an amino group, a $(C_1-C_4)$-alkylamino group, a di$(C_1-C_4)$-alkylamino group, a trifluoromethyl group, a —C(O)H group, a —C(O)CH$_3$ group, a —C(O)CF$_3$ group, a —Si(CH$_3$)$_3$ group, a —C(O)—NH$_2$ group, a $(C_1-C_4)$-hydroxyalkyl group or a $(C_2-C_4)$-dihydroxyalkyl group, providing that (i) R1 is not a 2-pyridyl group and (ii) R1 is not a 2-hydroxy-4-aminophenyl group.

\* \* \* \* \*